United States Patent [19]
Richelsoph

[11] Patent Number: 4,781,716
[45] Date of Patent: Nov. 1, 1988

[54] ARTIFICIAL HEART

[76] Inventor: Marc Richelsoph, Box 489-B, Nashville, Tenn. 37235

[21] Appl. No.: 14,362

[22] Filed: Feb. 13, 1987

[51] Int. Cl.⁴ .............................................. A61F 2/22
[52] U.S. Cl. .......................................... 623/3; 623/2; 417/412; 600/16
[58] Field of Search ........................ 623/3, 2; 128/1 D; 417/412, 413

[56] References Cited

U.S. PATENT DOCUMENTS

| | | | |
|---|---|---|---|
| 3,379,191 | 4/1968 | Harvey | 128/1 D |
| 4,058,855 | 11/1977 | Runge | 623/3 |
| 4,058,857 | 11/1977 | Runge et al. | 623/6 |
| 4,143,425 | 3/1979 | Runge | 623/3 |
| 4,143,661 | 3/1979 | LaForge et al. | 623/3 X |
| 4,173,796 | 11/1979 | Jarvik | 623/3 |
| 4,177,523 | 12/1979 | Lande | 623/3 |
| 4,576,606 | 3/1986 | Pol et al. | 623/3 |
| 4,665,896 | 5/1987 | La Forge et al. | 128/1 D |

FOREIGN PATENT DOCUMENTS 827070 5/1981 U.S.S.R. .................................. 623/3

OTHER PUBLICATIONS

"Design Criteria for Artificial Heart Valves", by T. Akutsu, The Journal of Thoracic & Cardiovascular Surgery, vol. 60, No. 1, Jul. 1970, pp. 34-45.

*Primary Examiner*—Ronald L. Frinks
*Attorney, Agent, or Firm*—Pitts and Brittian

[57] ABSTRACT

An improved artificial heart (10) for pumping blood. The artificial heart (10) comprises first and second pump units (12 and 14), each including a pump body (16) defining a collapsible bellows (18) and a fluid passageway (20) therethrough. Further, each pump body (16) has a first end portion (22) defining an outlet opening (30) and a second end portion (26) defining an inlet opening (32). Each of the first and second pump units (12 and 14) further comprises first and second valve units (24 and 28). The first valve unit (24) is secured to the first end portion (22) of the pump body (16) in fluid communication with the outlet opening (32), and includes a first one-way valve (38) for allowing blood to flow out of the pump body (16) and restricting the flow of blood into the pump body (16). The second valve unit (28) is secured to the second end portion (26) of the pump body (16) in fluid communication with the inlet openings (32), and includes a second one-way valve for allowing blood to flow into the pump body (16) and restricting the flow of blood out of the pump body (16). The artificial heart (10) also comprises drive means (61) for selectively collapsing and expanding the collapsible bellows (18) of the first and second pump units (12 and 14).

24 Claims, 5 Drawing Sheets

ARTIFICIAL HEART

DESCRIPTION

TECHNICAL FIELD

This invention relates to an improved artificial heart for pumping blood. In this particular invention, the artificial heart includes first and second pump units, each of which has a pump body defining a collapsible bellows.

BACKGROUND ART

Heretofore, the state-of-the-art artificial hearts have comprised rigid pumping chambers dissected by diaphragms such that a blood chamber and air chamber are defined. To accomplish the pumping operation, compressed air is vented into the air chamber causing the diaphragm to expand into the blood chamber forcing the blood out of the chamber. However, the turbulence generated by this pumping action and the compressing of the blood against the rigid surfaces of the pumping chamber damages the blood cells, often resulting in blood clotting. Moreover, such hearts are dependent upon exterior compressors to supply compressed air and, thus, are not self contained. Electrical drive means have been utilized in some artificial hearts, but such artificial hearts have still utilized either an expanding diaphragm to displace blood from a rigid chamber or a blood bladder which is compressed by a rigid member to displace the blood from the bladder. Of course, given the use of the rigid structure and the need for powerful drive means to accomplish the displacement of blood, not only is there damage to the blood cells, but the hearts tend to be heavy and large in size. Certain prior art artificial hearts are disclosed by U.S. Pat. Nos. 4,058,855, issued on Nov. 22, 1977; 4,173,796, issued on Nov. 13, 1979; and 4,576,606, issued on Mar. 18, 1986.

Therefore, it is an object of the present invention to provide an improved artificial heart for replacing a natural heart.

It is another object of the present invention to provide an improved artificial heart which minimizes damage to blood cells during the pumping operation.

Yet another object of the present invention is to provide an improved artificial heart which comprises a fully implantable, self-contained unit which can operate for extended periods without the necessity of an external power source.

Still another object of the present invention is to provide an artificial heart which simulates the pumping action of the natural heart, reproducing the diastolic and systolic pressures of natural heart function.

A further object of the present invention is to provide an artificial heart which is light weight and small in size.

Another object of the present invention is to provide an artificial heart which is inexpensive to manufacture and maintain.

DISCLOSURE OF THE INVENTION

Other objects and advantages will be accomplished by the present invention which provides an improved artificial heart for pumping blood. The artificial heart comprises first and second pump units, each including a pump body, defining a collapsible bellows and having a fluid passageway therethrough. Further, each pump body has a first end portion defining an outlet opening and a second end portion defining an inlet opening. Each of the first and second pump units further comprises first and second valve units. The first valve unit is secured to the first end portion of the pump body in fluid communication with the outlet opening, and includes a first one-way valve for allowing blood to flow out of the pump body and restricting the flow of blood into the pump body. The second valve unit is secured to the second end portion of the pump body in fluid communication with the inlet opening, and includes a second one-way valve for allowing blood to flow into the pump body and restricting the flow of blood out of the pump body. The artificial heart of the present invention also comprises drive means for selectively collapsing and expanding the bellows of the first and second pump units.

BRIEF DESCRIPTION OF THE DRAWINGS

The above-mentioned features of the present invention will become more clearly understood from the following detailed description of the invention read together with the drawings in which.

BEST MODE FOT CARRYING OUT THE INVENTION

An artificial heart incorporating various features of the present invention as illustrated at 10 in the figures. The heart 10 is designed to be implanted in a human or certain other mammals to replace a natural heart, and closely duplicates the pumping action of a natural heart, providing for a diastolic as well as a systolic pressure. Further, it will be understood from the following discussion that in the preferred embodiment, the heart 10 comprises a fully implantable self-contained unit which can operate for extended periods without the necessity of an external power source.

Figure 2:
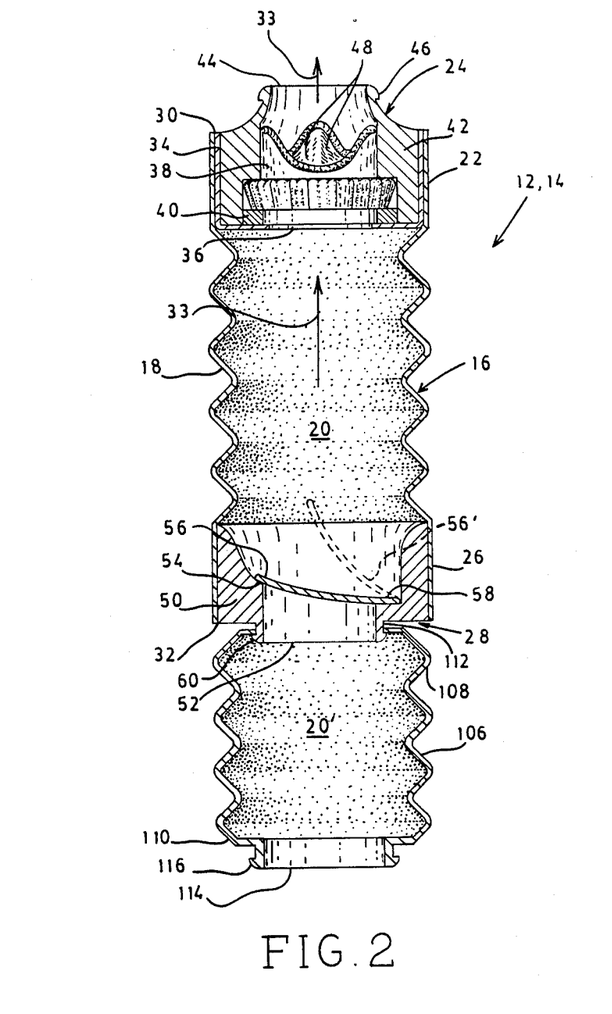
FIG. 2 illustrates a front view in section of one of the pump units of the artificial heart of the present invention.

Referring now to the figures, the heart 10 generally comprises a first or right pump unit 12 which serves to replace the right ventricle of the natural heart and a second or left pump unit 14 which serves to replace the left ventricle of the natural heart. Each of the pump units 12 and 14 are constructed alike; and, accordingly, in the figures and the discussion which follows, the various components of the pump units 12 and 14 will be provided with common reference numerals. As best illustrated in FIG. 2, each of the pump units 12, 14 includes a pump body 16 comprising a collapsible bellows 18 and defining a fluid passageway 20 therethrough. Further, the pump body 16 is provided with a first or upper end portion 22 for engaging a first or upper valve unit 24, and a second or lower end portion 26 for engaging a second or lower valve unit 28. More specifically, in the preferred illustrated embodiment, the first end portion 22 defines an outlet opening 30 for closely receiving the first valve unit 24 such that the valve unit 24 is housed in the first end portion 22 of the pump body 16. Similarly, the second end portion 26 defines an inlet opening 32 for closely receiving the second valve unit 28 such that the valve unit 28 is housed in the second end portion 26 of the pump body 16.

The pump body 16 is preferably fabricated of Biomer, a polyurethane compound produced by Ethicon Corporation. Biomer is flexible, durable and non-reactive to blood, and can be molded to produce surfaces smooth enough to prevent blood from clotting on the interior surfaces of the pump body 16. However, other suitably surgical quality materials having the requisite flexibility and durability can be utilized if desired.

As will be discussed in detail below, the pumping of blood is accomplished by the selective expanding and collapsing of the bellows 18, and in order to insure the proper direction of blood flow through the pump units 12 and 14, the valve units 24 and 28 accommodate flow only in one direction as indicated by the arrows 33. In this regard, the first or upper valve unit 24 serves to allow the flow of blood out of the first end portion 22 of the pump body 16, but does not allow blood to flow into the pump body 16. In the preferred embodiment, the valve unit 24 comprises a reinforcing ring 34 which is closely received in the first end portion 22 of the pump body 16. The reinforcing ring 34 is provided with an axial opening 36 which communicates with the passageway 20 of the pump body 16. A first one-way valve 38, supported upon an annular seal 40, is disposed above the opening 36 so as to intercept blood flow through the opening 36, with the valve 38 being held in place by a valve retainer 42 which is closely received in the reinforcing ring 34. As illustrated, the valve retainer 42 defines an outlet port 44 through which blood exits the pump unit 12, 14, with the mouth of the port 44 defining an annular securing lip 46.

Figure 4:
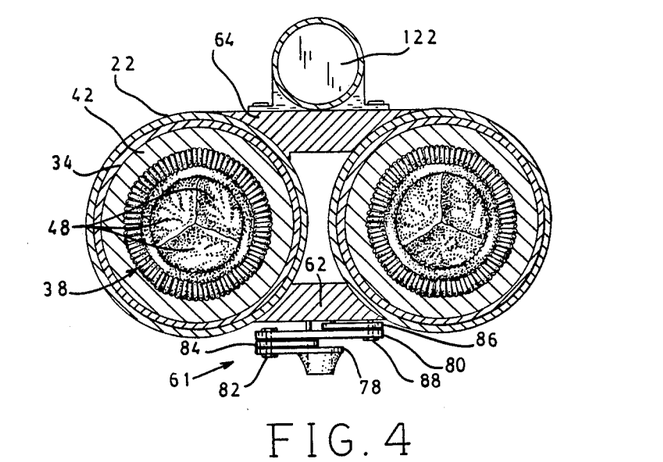
FIG. 4 illustrates a top view, in section at 4—4 of FIG. 3, of the artificial heart of the present invention.

In the preferred embodiment, and unlike prior art artificial hearts, the first one way valve 38 comprises a conventional natural tissue valve instead of an artificial valve. As illustrated in FIG. 4, the valve 38 has three leaves 48 of natural tissue such as porcine (pig heart valve) or pericardial xenograft (calf pericardial tissue). The leaves 48 are mounted in the valve 38 such that they open outwardly, but collapse together and seal the valve in response to fluid pressure in the opposing direction, thereby prohibiting blood flow into the pump body. The capability of the heart 10 to utilize tissue valves reduces the chance of blood clots forming on the valves which is common where artificial valves are utilized. It will be noted, however, that various conventional artificial valves can be utilized in the valve unit 38, if desired.

The second valve unit 28 also comprises a one-way valve and serves to allow blood to flow into the pump body 16 through the second end portion 26, and prohibits blood flow out of the body 16. In the preferred embodiment, the valve unit 28 comprises a valve body 50 which is closely received and housed in the second end portion 26 of the pump body 16. The valve body 50 defines an inlet port 52 communicating with the passageway 20 of the pump body 16 and defines an annular valve seat 54 circumscribing the interior mouth of the port 52. A flexible valve leaf 56 is secured to the valve body 50 as illustrated at 58 in FIGS. 2 and 5 so as to engage the valve seat 54. As illustrated by the broken lines at 56′, the leaf 56 flexes inward to allow blood flow into the pump body 16, but prohibits flow out of the pump body 16 by seating against the valve seat 54 and sealing the inlet port 52. It will also be noted that the exterior mouth of the inlet port 52 defines an annular securing lip 60 which will be discussed below.

In the preferred embodiment, the valve body 50 is fabricated of Teflon and coated with Biomer, and the leaf 56 is fabricated of a reinforced polymer coated with Biomer and bonded to the body 50 with Biomer so as to eliminate any seams where blood clotting might occur. Of course, other surgical quality fabricating materials can be utilized if desired. Further, as with the first valve unit 24, various conventional artificial heart valves can be utilized, and the illustrated valve unit 28 is simply one preferred embodiment.

In light of the above, it will be understood that as the bellows 18 is collapsed, the leaf 56 seats against the valve seat 54 prohibiting blood flow out of the inlet port 52, and the decreasing volume of the passageway 20 causes blood within the passageway to be forced through the first one-way valve 38 and the outlet port 44. As the bellows 18 is expanded, the one-way valve 38 closes and blood is drawn into the passageway 20. Thus, by continuously contracting and expanding the bellows 18, a continuous pumping action is achieved, thereby mimicking the function of a ventricle of a natural heart.

Figure 3:
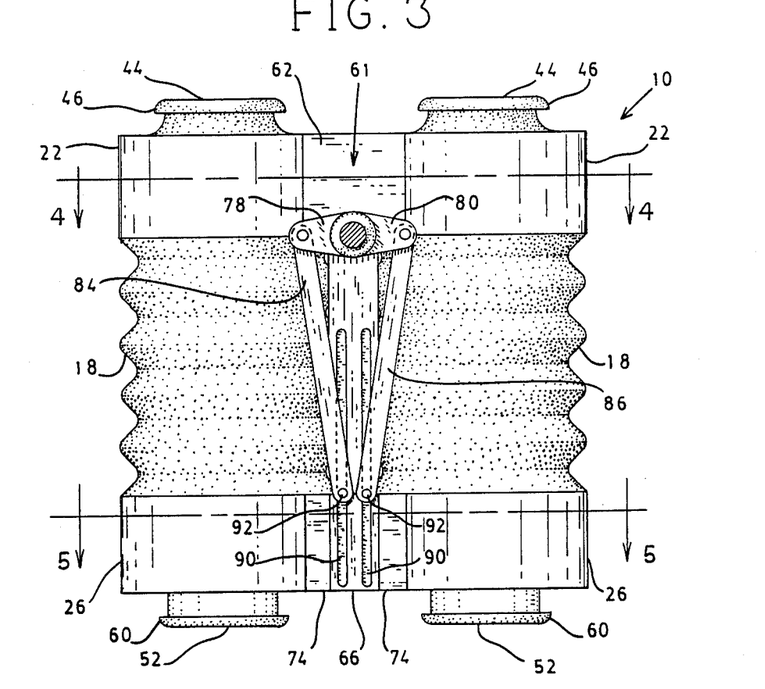
FIG. 3 illustrates a front view of the artificial heart of the present invention.
Figure 5:
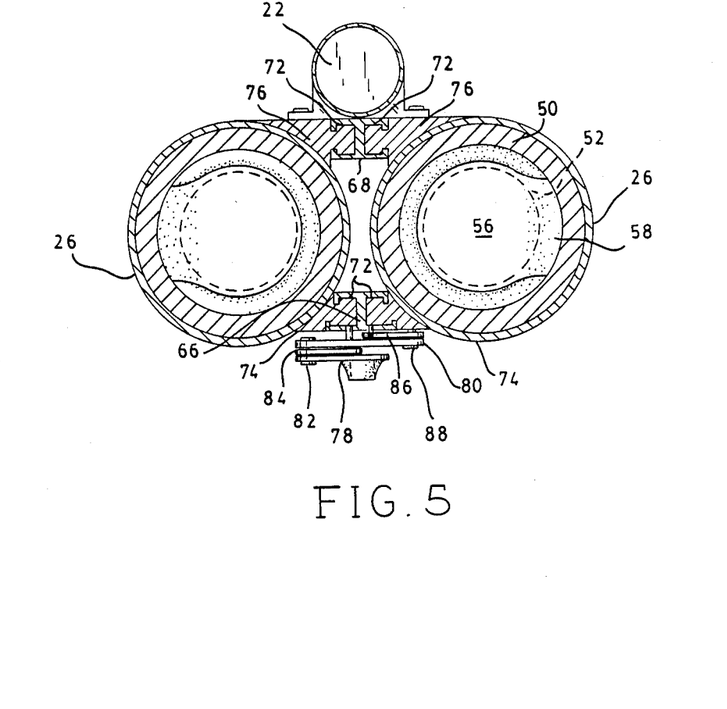
FIG. 5 illustrates a top view, in section at 5—5 of FIG. 3, of the artificial heart of the present invention.

Referring now to FIGS. 3, 4, and 5, the artificial heart 10 is provided with a pump drive means 61 for selectively collapsing and expanding the bellows 18 of the pump units 12 and 14. In order to facilitate the operation of both of the units 12 and 14 with a single drive means, the drive means 61 comprises a pair of bracket members 62 and 64 which serve to secure the pump units 12 and 14 together proximate the first end portions 22, in substantially parallel alignment. The bracket members 62 and 64 carry downwardly extending guide arms 66 and 68, respectively, which extend to a point proximate the second end portions 26 of the pump bodies 16. Further, both of the guide arms 66 and 68 define oppositely disposed guide receptor slots 72 which slidably receive the guide members 74 and 76 which are mounted on the pump units 12 and 14 proximate the second end portions 26. Thus, it will be appreciated that whereas the first end portion 22 of the units 12 and 14 are fixedly secured together, the second end portions are slidably and independently secured to the guide arms 66 and 68 so as to be capable of the axial travel necessary to accommodate the collapsing and expanding of the bellows 18.

The drive means 61 further comprises a motor 70 (see FIG. 1), preferably a brushless D.C. motor, disposed between, and secured to, the pump units 12 and 14 proximate the first end portions 22. An eccentric cam assembly is provided to impart the desired reciprocal motion for driving the bellows 18. The cam assembly comprises first and second cam members 78 and 80, respectively, the first cam 78 being secured to the drive shaft of the motor 70, and the second cam 80 being secured to the first cam 78 with a mounting pin 82 as illustrated in FIG. 4. Also, as illustrated in FIG. 4, a first push/pull rod 84 is rotatably mounted on the pin 82 between the cams 78 and 80; and a second push/pull rod 86 is rotatably secured to the second cam 80 with the mounting pin 88. Given that the axes of the mounting pins 82 and 88 are displaced from the axis of the drive shaft of the motor 70, it will be appreciated by those skilled in the art that rotation of the drive shaft imparts reciprocal motion to the push/pull rods 78 and 80. As best illustrated in FIG. 3, the guide arm 66 is provided with a pair of elongated slots 90 opening into the guide receptor slots 72, allowing the outboard end portions 92 of the push/pull rods 84 and 86 to be pivotally secured to the guide mebers 74 of the pump units 12 and 14. Thus, the outboard end portions of the push/pull rods 84 and 86 being secured to the second end portions 26 of the pump units 12 and 14, reciprocal travel of the rods 84 and 86 causes the bellows 18 to collapse and expand.

It will be noted that the cams 78 and 80 are oriented such that the mounting pins 82 and 88 are disposed on opposite sides of the drive shaft of the motor 70. Accordingly, as the rod 84 is collapsing the bellows 18 of the unit 14, the rod 86 is expanding the bellows of the unit 12. (See FIG. 1.) This insures that, given the closed nature of the circulatory system, the pump units 12 and 14 are not working against one another, and provides for a close simulation of the diastolic and systolic pressures produced by the natural heart. For example, as the pump unit 12 pumps blood into the pulmonary artery leading to the lungs through contraction of the operatively associated bellows 18, the pump unit 14 is cooperatively drawing in oxygenated blood from the lungs through expansion of the operatively associated bellows 18. Of course, the illustrated drive means 61 is only one preferred means for accomplishing this cooperative collapsing and expanding of the bellows 18, and other suitable means may be used if desired.

Referring once again to FIG. 1, it will be appreciated by those skilled in the art that when the heart 10 is implanted, the outlet ports 44 of the pump units 12 and 14 are placed in fluid communication with the pulmonary artery 94 and the aorta 96, and the inlet ports 52 are placed in fluid communication with the vena cava 98 and the pulmonary vein 100. With respect to the connection of the outlet ports 44 to the great arteries, conventional arterial prosthesis 102 can be used. Each prosthesis 102 is anastomosed to the associated artery and the outboard end portion 104 is snap fitted over the mouth of the outlet port 44 and retained in place by the securing lip 46.

Figure 1:
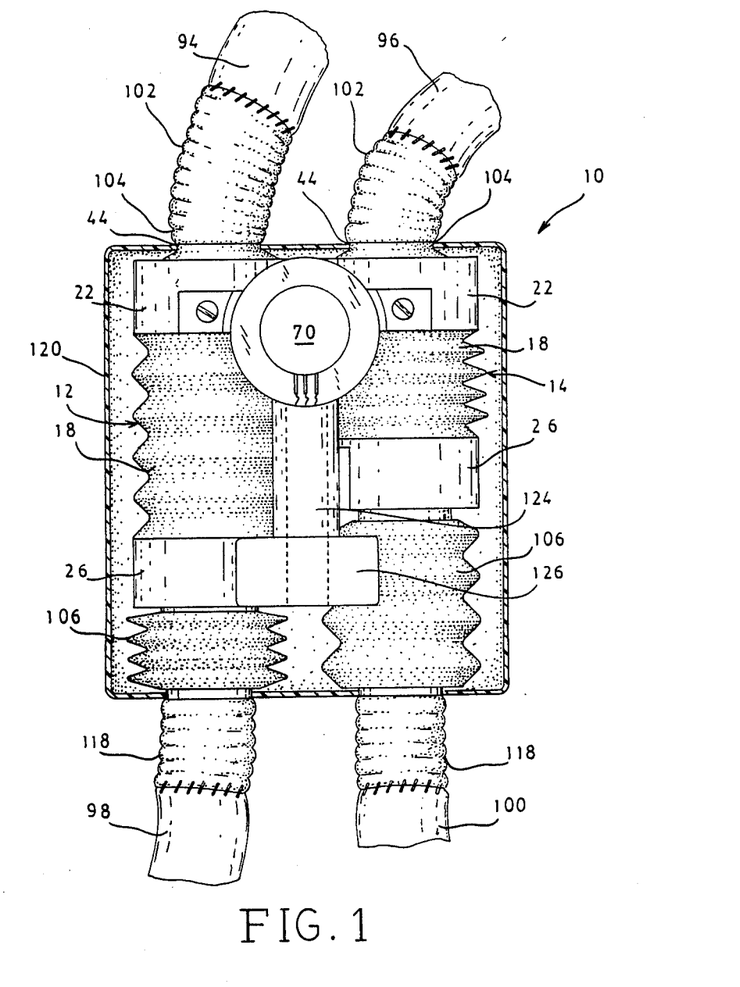
FIG. 1 illustrates a front view of the artificial heart of the present invention.

With respect to the connecting of the inlet ports 52, and given the reciprocation of the second end portions 26 of the pump units 12 and 14, the preferred embodiment of the heart 10 is provided with a pair of interfacing bellows 106. Each of the interfacing bellows 106 has a first end portion 108 and a second end portion 110 and defines a fluid passageway 20' therethrough. The first end portion 108 defines an outlet opening 112 which snap fits around the mouth of the inlet port 52 and is held in place by the securing lip 60. The second end portion 110 defines an inlet port 114 circumscribed by a mouth portion carrying a securing lip 116. As illustrated in FIG. 1, the bellows 106 interface between the inlet ports 52 and the venous structures, and each bellows 106 is expanded and collapsed by the movement of the associated second end portion 26; expanding as the operatively associated bellows 18 is collapsed and collapsing as the operatively associated bellows 18 is expanding. Accordingly, the bellows 106 insure that no undue stress is exerted on the venous structures through the reciprocal travel of the second end portions 26 of the pump units 12 and 14. Further, whereas the prevailing surgical procedure for implanting an artificial heart involves removal of only the natural ventricles and connection of the inlet ports to the natural heart atria, the bellows 106 serve as prosthetic atria, allowing the natural atria to be surgically removed. Accordingly, as illustrated in FIG. 1, the vena cava 98 and the pulmonary vein 100 are connected to the inlet port 114 with conventional prostheses 118, the prostheses 118 being anastomosed to the vena cava 98 (the superior and inferior vena cava having been surgically joined) and the pulmonary vein 100, and snap fitted on the inlet ports 114 as described with respect to the arterial prostheses 102. Of course, if desired, conventional surgical procedures can be followed whereby the natural atria are left. In this event conventional atrial cups (not shown) are anastomosed to the natural atria and snap fitted on the inlet ports 114.

In FIG. 1, it will be noted that in the preferred embodiment, the heart 10 further comprises a fluid impervious external case 120, preferably fabricated of Biomer, for housing the pump units 12 and 14, and the drive means 61. It will also be noted that the case 120 houses a rechargable battery 122 (see FIG. 4), a backup battery 124,, and electrical control means 126. The rechargable battery 122 is designed to be the primary power supply for the motor 70, and allows the heart 10 to function independent of an external power source. Recharging of the battery 122 in the preferred embodiment is accomplished by the use of a split transformer (not shown) of conventional design. One coil of the transformer is implanted in the body. The cooperating coil is placed at a location exterior to the body but proximate the implanted coil. Inductive coupling of these coils serves to produce the recharging current within the implanted coil. The backup battery 124 is designed to provide a power supply for a limited period of time should the battery 122 be drained or fail. The electrical control means 126 measures and, by controlling the operation of the motor 70, keeps constant the systolic pressure in the cardiovascular system. In this regard, the cardiovascular system dilates and constricts in response to such things as whether the body is exercising or is at rest, and the natural heart rate increases or decreases in response to such dilation and constriction. Accordingly, the control means 126 monitors pressure within the cardiovascular system, and either increases or decreases the pumping rate of the heart 10 as needed to maintain a substantially constant blood pressure. A schematic diagram of one suitable control means 126 is set forth in FIG. 6.

Figure 6:
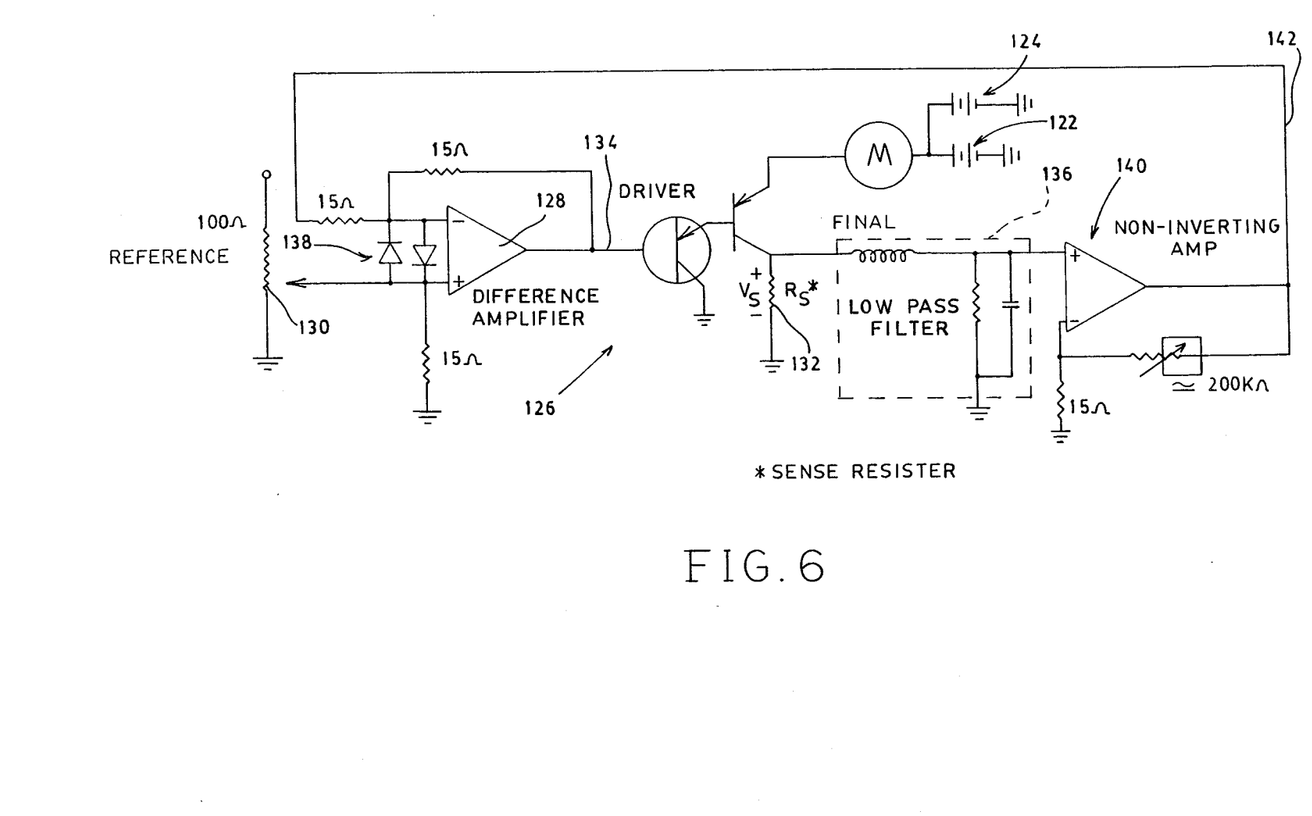
FIG. 6 is a schematic diagram of one suitable electrical control means for the artificial heart of the present invention.

The circuit, as shown in FIG. 6, is the motor driving and regulating system or electrical control means 126. The basis of the control means 126 is set down by a law called Starling's Law. The body is generally maintained at a constant pressure. If the pressure drops within the body, the heart must increase in beats to increase the pressure. If the pressure increases, the heart must slow down. The circuit, or control means 126, is designed to take advantage of these principles. More specifically, the circuit 126 works using a differencing amplifier 128 to compare a reference voltage generated at resistor 130 to the sense resistor voltage ($V_s$, and then use this information to adjust the voltage on the driver transistor's base 134. The motor draws current through $R_s$, thus the voltage across $R_s$ is a direct indication of motor output. The basis of the circuit is to keep $V_s$ (across $R_s$) constant. Constant current is constant torque. The voltage does, however, change and varies in order to maintain constant current. A low pass filter 136 has been added to the circuit to reduce AC and noise coming from the DC motor 70. The diodes 138 prevent the circuit from abruptly forcing the motor 70 to the correct current. It will also be noted that a non-inverting amplifier 140 has been added to the feedback loop 142 of the difference amplifier 128 in the preferred embodiment.

In light of the above, it will be appreciated that the artificial heart 10 is a great improvement over the prior art. Unlike the prior art artificial hearts, the pump body 16 of the heart 10 is smooth and flexible obviating the damage done to the blood in prior art hearts by blood being compressed against hard surfaces, and also allowing the heart 10 to be lighter in weight and smaller in size. The linear blood flow through the heart 10 reduces turbulence, further reducing damage to the blood which might precipitate clotting. Moreover, the heart 10 can utilize a variety of conventional heart valves, including a natural tissue valve for the upper valve 38, and, the heart 10 is a fully implantable heart requiring only periodic recharging to remain operational.

While a preferred embodiment has been shown and described, it will be understood that there is no intent to limit the invention to such disclosure, but rather it is intended to cover all modifications and alternate constructions falling within the spirit and scope of the invention as defined in the appended claims.

I claim:

1. An improved artificial heart for pumping blood, said heart comprising:

first and second pump units, each said first and second pump unit including a pump body defining an axially collapsible bellows of substantially cylindrical shape and having a coaxial fluid passageway therethrough, said pump body having a first end portion defining an outlet opening and an oppositely disposed second end portion defining an inlet opening, whereby substantially linear flow of said blood through said fluid passageway from said inlet opening to said outlet opening is achieved, said first and second pump units each having a first valve unit secured to said first end portion of said pump body in fluid communication with said outlet opening, said first valve unit including a first one-way valve for allowing said blood to flow out of said pump body and restricting the flow of said blood into said pump body, each said first and second pump unit also having a second valve unit secured to said second end portion of said pump body in fluid communication with said inlet opening, said second valve unit including a second one-way valve for allowing said blood to flow into said pump body and restricting the flow of said blood out of said pump body; and drive means for selectively collapsing and expanding said bellows of said first and second pump units.

2. The improved artificial heart of claim 1 wherein said first valve unit of each said pump unit is closely received and housed in said first end portion of said pump body and said second valve unit of each said pump unit is closely received and housed in said second end portion of said pump body.

3. The improved artificial heart of claim 1 wherein said first one-way valve of each said pump unit comprises a natural tissue valve.

4. The improved artificial heart of claim 1 wherein each said second valve unit comprises a valve body for being closely received in said second end portion of said pump body, said valve body defining an inlet port communicating with said passageway of said pump body, said inlet port defining an interior mouth defining a valve seat and an exterior mouth carrying a securing lip, said valve unit further comprising a flexible leaf secured to said valve body adjacent said interior mouth of said inlet port for selectively seating against said valve seat and covering said inlet port.

5. The improved artificial heart of claim 1 wherein each said second valve unit defines an inlet port through which said blood is received into said passageway of said pump body, and wherein each said pump unit is provided with a cooperating interfacing bellows secured to said inlet port of said second valve unit in fluid communication, for communicating said blood to said inlet port while accommodating the collapse and expansion of said collapsible bellows, whereby said interfacing bellows expand as said collapsible bellows collapse and collapse as said collapsible bellows expand thereby simulating the functioning of the atria of a natural heart.

6. The improved artificial heart of claim 3 wherein each said second valve unit comprises a valve body for being closely received in said second end portion of said pump body, said valve body defining an inlet port communicating with said passageway of said pump body, said inlet port defining an interior mouth defining a valve seat and an exterior mouth carrying a securing lip, said valve unit further comprising a flexible leaf secured to said valve body adjacent said interior mouth of said inlet port for selectively seating against said valve seat and covering said inlet port.

7. The improved artificial heart of claim 6 wherein each said second valve unit defines an inlet port through which said blood is received into said passageway of said pump body, and wherein each said pump unit is provided with a cooperating interfacing bellows secured to said inlet port of said second valve unit in fluid communication, for communicating said blood to said inlet port while accommodating the collapse and expansion of said collapsible bellows, whereby said interfacing bellows expand as said collapsible bellows collapse and collapse as said collapsible bellows expand thereby simulating the functioning of the atria of a natural heart.

8. An improved artificial heart for pumping blood, said heart comprising:

first and second pump units, each said first and second pump unit including a pump body defining a collapsible bellows and having a fluid passageway therethrough, said pump body having a first end portion defining an outlet opening and a second end portion defining an inlet opening, said first and second pump units each having a first valve unit secured to said first end portion of said pump body in fluid communication with said outlet opening, said first valve unit including a first one-way valve for allowing said blood to flow out of said pump body and restricting the flow of said blood into said pump body, each first and second pump unit also having a second valve unit secured to said second end portion of said pump body in fluid communication with said inlet opening, said second valve unit including a second one-way valve for allowing said blood to flow into said pump body and restricting the flow of said blood out of said pump body;

at least one bracket member for engaging said first and second pump units proximate aid first end portions, for securing said first and second pump units in substantially parallel alignment, said bracket member carrying a guide arm extending toward said second end portions of said pump units, said guide arm defining a pair of oppositely disposed guide receptor slots, and wherein each said first and second pump unit is provided with at least one guide member proximate said second end portion for being slidably received in one said guide receptor slot; and drive means for selectively collapsing and expanding said bellows of said first and second pump units.

9. The improved artificial heart of claim 8 wherein said heart is provided with a first and second said bracket member and each said pump unit is provided with a pair of said guide members.

10. The improved artificial heart of claim 8 wherein said first valve unit of each said pump unit is closely received and housed in said first end portion of said pump body and said second valve unit of each said pump unit is closely received and housed in said second end portion of said pump body.

11. The improved artificial heart of claim 8 wherein said first one-way valve of each said pump unit comprises a natural tissue valve.

12. The improved artificial heart of claim 8 wherein each said second valve unit comprises a valve body for being closely received in said second end portion of said pump body, said valve body defining an inlet port communicating with said passageway of said pump body, said inlet port defining an interior mouth defining a valve seat and an exterior mouth carrying a securing lip, said valve unit further comprising a flexible leaf secured to said valve body adjacent said interior mouth of said inlet port for selectively seating against said valve seat and covering said inlet port.

13. The improved artificial heart of claim 8 wherein each said second valve unit defines an inlet port through which said blood is received into said passageway of said pump body, and wherein each said pump unit is provided with an interfacing bellows secured to said inlet port of said second valve unit in fluid communication, for communicating said blood to said inlet port while accommodating the collapse and expansion of said collapsible bellows.

14. The improved artificial heart of claim 8 wherein said artificial heart comprises a fluid impervious case for housing said first and second pump units and said drive means.

15. An improved artificial heart for pumping blood, said heart comprising:

first and second pump units, each said first and second pump unit including a pump body defining a collapsible bellows and having a fluid passageway therethrough, said pump body having a first end portion defining an outlet opening and a second end portion defining an inlet opening, said first and second pump unit each having a first valve unit secured to said first end portion of said pump body in fluid communication with said outlet opening, said first valve unit including a first one-way valve for allowing said blood to flow out of said pump body and restricting the flow of said blood into said pump body, each said first and second pump unit also having a second valve unit secured to said second end portion of said pump body in fluid communication with said inlet opening, said second valve unit comprising a second one-way valve for allowing said blood to flow into said pump body and restricting the flow of said blood out of said pump body; and drive means for selectively collapsing and expanding said bellows of said first and second pump units, said drive means comprising a motor mounted on said first and second pump unit, said motor including a selectively rotatable drive shaft carrying an eccentric cam assembly, said cam assembly comprising a pair of oppositely disposed first and second cam members, said first cam member rotatably carrying a first push/pull rod, and said second cam member rotatably carrying a second push/pull rod, said first push/pull rod having an outboard end portion pivotally secured to said first pump unit proximate said second end portion, and said second push/pull rod having an outboard end portion secured to said second pump unit proximate said second end portion.

16. The improved artificial heart of claim 15 wherein said artificial heart comprises at least one bracket member for engaging said first and second pump units proximate said first end portions for securing said first and second pump units in substantially parallel alignment, said bracket member carrying a guide arm extending toward said second end portions, said guide arm defining a pair oppositely disposed guide receptor slots, and wherein each said first and second pump unit is provided with at least one guide member proximate said second end portion for being slidably received in one said guide slot.

17. The improved artificial heart of claim 16 wherein said guide arm comprises a pair of first and second elongated guide pin slots accessing said guide receptor slots, and wherein said outboard end portion of said first push/pull rod carries a guide pin for being received through said first guide pin slot and engaging said guide member of said first pump unit, and said outboard end portion of said second push/pull rod carries a guide pin for being received through said second guide pin slot and engaging said guide member of said second pump unit.

18. The improved artificial heart of claim 17 wherein said first one-way valve of each said pump unit comprises a natural tissue valve.

19. The improved artificial heart of claim 15 wherein each said second valve unit comprises a valve body for being closely received in said second end portion of siad pump body, said valve body defining an inlet port ocmmunicating with said passageway of said pump body, said inlet port defining an interior mouth defining a valve seat and an exterior mouth carrying a securing lip, said valve unit further comprising a flexible leaf secured to said valve body adjacent said interior mouth of said inlet port for selectively seating against said valve seat and covering said inlet port.

20. The improved artificial heart of claim 15 wherein said drive means further comprises a rechargeable battery for supplying power to said motor.

21. An improved artificial heart for pumping blood, said heart comprising:

first and second pump units, each said first and second pump unit including a pump body defining a collapsible bellows and having a fluid passageway therethrough, said pump body having a first end portion defining an outlet opening and a second end portion defining an inlet opening, said first and second pump units each having a first valve unit secured to said first end portion of said pump body in fluid communication with said outlet opening, said first valve unit including a first one-way valve for allowing said blood to flow out of said pump body, each first and second pump unit also having a second valve unit secured to said second end portion of said pump body in fluid communication with said inlet opening, said second valve unit including a second one-way valve for allowing said blood to flow into said pump body and restricting the flow of said blood out of said pump body; and drive means for selectively collapsing and expanding said bellows of said first and second pump units, said drive means having a motor mounted on said first and second pump units, said motor including a selectively rotatable drive shaft carrying an eccentric cam assembly, said cam assembly comprising a pair of oppositely disposed first and second cam members, said first cam member rotatably carrying a first push/pull rod, and said second cam member rotatably carrying a second push/pull rod, said first push/pull rod having an outboard end portion pivotally secured to said first pump unit proximate said second end portion, and said second push/pull rod having an outboard end portion pivotally secured to said second pump unit proximate said second end portion.

22. The improved artificial heart of claim 21 wherein said drive means further comprises a rechargable battery for supplying power to said motor.

23. The improved artificial heart of claim 21 wherein said artificial heart comprises a second backup battery for supplying power to said motor.

24. The improved artificial heart of claim 21 wherein said artificial heart further comprises electrical control means for controlling said motor so as to maintain a preselected fluid pressure within siad pump units.

* * * * *

UNITED STATES PATENT AND TRADEMARK OFFICE
CERTIFICATE OF CORRECTION

PATENT NO. : 4,781,716
DATED : November 1, 1988
INVENTOR(S) : Marc Richeksoph

It is certified that error appears in the above-identified patent and that said Letters Patent is hereby corrected as shown below:

At Column 2, line 37, "FOT" should read --FOR--.

At Column 12, line 14, "siad" should read --said--.

Signed and Sealed this

Thirtieth Day of May, 1989

Attest:

DONALD J. QUIGG

Attesting Officer

Commissioner of Patents and Trademarks